(12) United States Patent
Crichton et al.

(10) Patent No.: US 10,195,633 B2
(45) Date of Patent: Feb. 5, 2019

(54) SEPARABLE MEMBRANE IMPROVEMENTS (75) Inventors: Daniel Crichton, Cambridge (GB); Robert Gordon Maurice Selby, Melbourn (GB); David Martin Pooley, Stapleford (GB)

(73) Assignee: THE TECHNOLOGY PARTNERSHIP PLC (GB)

(*) Notice: Subject to any disclaimer, the term of this patent is extended or adjusted under 35 U.S.C. 154(b) by 457 days.

(21) Appl. No.: 14/118,010

(22) PCT Filed: May 16, 2012

(86) PCT No.: PCT/GB2012/051081
§ 371 (c)(1),
(2), (4) Date: Nov. 15, 2013

(87) PCT Pub. No.: WO2012/156724
PCT Pub. Date: Nov. 22, 2012

(65) Prior Publication Data
US 2014/0110500 A1 Apr. 24, 2014

(30) Foreign Application Priority Data
May 16, 2011 (GB) .................. 1108102.3

(51) Int. Cl.
*B05B 17/00* (2006.01)
*A61M 11/00* (2006.01)

(52) U.S. Cl.
CPC ........ *B05B 17/0646* (2013.01); *A61M 11/005* (2013.01)

(58) Field of Classification Search
CPC ........... B05B 17/04–17/0692; A61M 15/0085; A61M 11/005

USPC ................. 239/102.1, 102.2; 128/200.14
See application file for complete search history.

(56) References Cited

U.S. PATENT DOCUMENTS

| 3,561,444 | A |   | 5/1971  | Boucher |
| 3,812,854 | A | * | 5/1974  | Michaels et al. ........ 128/200.16 |
| 4,533,082 | A | * | 8/1985  | Maehara et al. .......... 239/102.2 |
| 4,702,418 | A |   | 10/1987 | Carter et al. |
| 5,152,456 | A | * | 10/1992 | Ross et al. ................. 239/102.2 |
| 5,518,179 | A | * | 5/1996  | Humberstone et al. ... 239/102.2 |
| 5,838,350 | A |   | 11/1998 | Newcombe et al. |

(Continued)

FOREIGN PATENT DOCUMENTS

| EP | 1475108 | 5/2004 |
| WO | 9310910 | 6/1993 |

(Continued)

OTHER PUBLICATIONS

Hi Temp Metals, Permendur 2V (Hiperco 50A) Technical Data, May 12, 2004, <http://www.hightempmetals.com/techdata/hitempPermendurdata.php.*

*Primary Examiner* — Alexander Valvis
*Assistant Examiner* — Cody Lieuwen
(74) *Attorney, Agent, or Firm* — Tarolli, Sundheim, Covell & Tummino LLP (57) ABSTRACT

A liquid droplet production apparatus includes a perforate membrane, with liquid being supplied to one side of the membrane. An actuator for vibrating the membrane is provided. The vibration causes liquid droplets to be ejected from the other side of the membrane. Magnetic force is used to connect the actuator to the membrane so that the vibration can be transmitted.

21 Claims, 9 Drawing Sheets

(56) References Cited

U.S. PATENT DOCUMENTS

| | | | |
|---|---|---|---|
| 6,227,853 B1* | 5/2001 | Hansen et al. | 433/119 |
| 6,805,301 B2* | 10/2004 | Garcia | 239/102.2 |
| 2004/0050947 A1* | 3/2004 | Power et al. | 239/4 |
| 2008/0308096 A1* | 12/2008 | Borgschulte et al. | 128/200.14 |
| 2011/0266359 A1* | 11/2011 | Haran | 239/6 |
| 2012/0285446 A1* | 11/2012 | Van Der Mark | 128/200.14 |

FOREIGN PATENT DOCUMENTS

| | | |
|---|---|---|
| WO | 0047128 | 8/2000 |
| WO | 2006006963 | 1/2006 |
| WO | 2009136309 | 11/2009 |
| WO | 2009150619 | 12/2009 |
| WO | 2010026532 | 3/2010 |
| WO | 2011083379 | 7/2011 |
| WO | 2011083380 | 7/2011 |

\* cited by examiner

(a) External support (b) Multiple contact surfaces (c) Example force profile

(a) Dose capsules:

Actuator:

Actuator + Dose Capsule:

SEPARABLE MEMBRANE IMPROVEMENTS

FIELD OF THE INVENTION

This invention relates to electronic spray devices in which a vibrating perforate membrane is used to generate liquid droplets; in particular, to how such devices can be made more useful by enabling the separation of the vibrating membrane from its driver element.

According to a first aspect of the invention, there is provided a liquid droplet production apparatus comprising a perforate membrane; a means for supplying liquid to one side of the membrane: an actuator for vibrating the membrane said vibration causing liquid droplets to be ejected from the other side of the membrane; in which magnetic force is used to connect the actuator to the membrane so that the vibration can be transmitted.

BACKGROUND OF THE INVENTION

Introduction & Prior Art on Separable Membrane Technology

Electronic nebulisers that use ultrasonic vibration to generate liquid droplets are well known in the art and have found use in a wide range of fields including medical drug delivery and the treatment of air (for example fragrance delivery and humidification). A subset of such devices in widespread use (commonly referred to as 'pond misters') use a vibrating surface covered by liquid to cause droplets to be generated through the break-up of standing waves on the liquid free surface (U.S. Pat. No. 3,812,854 being an example). This break-up leads to droplets with a wide range of sizes being produced and shaping of the liquid container above the level of the liquid is used to limit the size range of droplets that escape and are delivered. With a wide range of droplets being contained and returned to the bulk liquid, such devices have low efficiency resulting in high power consumption. The efficiency of such devices can be improved by constraining the free surface of the liquid with a perforate membrane (U.S. Pat. No. 4,533,082 for example). This membrane may have just a single nozzle (for dispensing or printing applications for example in which individual drops may be dispensed on demand) or may have many thousand nozzles (for nebuliser applications for example). Relatively monodispersed droplets are produced when such perforate membranes are used in which the droplet diameter is related to the size of the openings, or nozzles, in the perforate membrane. Such devices still suffer multiple disadvantages: In particular, the vibrating surface needs to be mounted close to the membrane, but not touching, for effective droplet generation and not all liquid in the container can be delivered (as the liquid is required to transmit the pressure waves to the perforate membrane). A preferred embodiment of such devices is therefore one in which the perforate membrane itself is vibrated by the driver element (commonly called the actuator) with examples including U.S. Pat. No. 4,533,082 and EP 0431992. This enables the delivery of relatively well monodispersed droplets without requiring the pressure waves to be transmitted through a liquid layer further increasing efficiency and enabling a wider range of embodiments. A preferred embodiment of such a device such as described in U.S. Pat. No. 5,518,179 uses a bending mode actuator to deliver the vibrational energy to the membrane as this enables the use of thin low cost actuators and further increases efficiency.

Often it is desirable to use a master-cartridge model in which a master unit can spray liquid contained in a replaceable cartridge. Preferably, all liquid contacting components reside on the cartridge and as many non-liquid contacting components as possible reside on the master. This minimises the cost of the cartridge whilst avoiding liquid cross-contamination between cartridges and liquid contamination of the master. Examples of fields where such an approach finds use are the medical field and the consumer fragrance field. In the medical field dose sterility can be critical and this can be achieved by containing each dose in its own cartridge (or capsule). Also in the medical field the same master device may be designed to be used with more than one patient and cross-contamination should be avoided. In the fragrance field, each cartridge may contain a different fragrance and again cross-contamination should be avoided. Other fields in which similar requirements are met will be obvious to someone skilled in the art.

One approach to avoid cross contamination is to place the perforate membrane and actuator into the cartridge component with the electronics and power source in the master. This limits the required connection between the two components to electrical but, with the actuator in the cartridge, leaves a relatively high cost component in the cartridge. Further, and more importantly for medical applications where each cartridge contains a single dose, the cartridge size may be relatively large compared to the amount of liquid it contains. There is therefore a need to move the actuator out of the cartridge component leaving just the liquid contacting perforate membrane as this approach can reduce both cartridge cost and size.

The requirement to avoid cross contamination is known in the art and, for relatively inefficient applications where low power consumption is not crucial, solutions have been proposed. U.S. Pat. No. 3,561,444 teaches, for a pond-mister style device, using a liquid that is not dispensed to provide the connection between the vibration element in the master and the surface to be vibrated in the cartridge. U.S. Pat. No. 4,702,418, WO 2006/006963, WO 2009/150619, WO 2010/026532 and WO 2009/136304 teach various means of connecting the vibration force to a surface in the cartridge that is situated in close proximity to a perforate membrane with the vibration then transmitted through the liquid to be sprayed. EP 1,475,108 and U.S. Pat. No. 5,838,350 teach coupling of a piezoceramic component directly to a perforate membrane but do not teach how this can be done in an efficient manner or without the connection approach resulting in excessive energy absorption. The Büchi B-90 Nano Spray Drier enables the perforate membrane to be replaced by requiring the user to screw the membrane onto the actuator using a custom nut to a specified torque level. Whilst this is suitable for a laboratory instrument the replacement process is hard to automate in a compact device it would not be acceptable for a device that is designed to be operated by a consumer for example.

Efficient connection of energy is even more critical for low power devices and in particular for devices where the actuator operates in bending mode as in U.S. Pat. No. 5,518,179. Further, efficient connection of energy through a bending interface is significantly more challenging than efficient connection of energy through a translating interface. This is because a torque in addition to a normal force must be transmitted and also because any structures that result in the device becoming thicker (a screw thread for example) reduce vibration.

In summary, there is a requirement for a means to enable vibration to be effectively transmitted from an actuator to a perforate membrane in which the perforate membrane can be easily removed and replaced by a non-skilled consumer or automatically within a compact device. Such transmission would ideally not absorb excessive vibration energy. Such transmission would ideally not reduce the vibration amplitude of the perforate membrane. These preferable requirements are especially challenging with bending-mode actuator devices as they are more easily damped.

SUMMARY OF THE INVENTION

Therefore, according to a first aspect of the invention, there is provided a liquid droplet production apparatus comprising a perforate membrane; a means for supplying liquid to one side of the membrane; an actuator for vibrating the membrane said vibration causing liquid droplets to be ejected from the other side of the membrane, in which magnetic force is used to connect the actuator to the membrane so that the vibration can be transmitted.

Generally Applicable Actuator Design and Mounting

This invention is applicable to a wide range of actuator types but is of particular benefit to actuators that use a piezoelectric, electrostrictive or magnetostrictive material (i.e. a material that changes shape in response to an applied electric or magnetic field, henceforth referred to as the active component) in combination with a metal connection or support material (henceforth referred to as the passive component). Examples of such actuators include longitudinal actuators which drive the perforate membrane to vibrate in a direction generally parallel to the expansion and contraction direction of the active component, breathing mode actuators which drive the perforate membrane to vibrate in a direction generally normal to the expansion and contraction direction of the active component and bending mode actuators of the type described earlier and in more detail in U.S. Pat. No. 5,518,179, incorporated herein for reference, to which this invention is particularly applicable. Whilst for some actuators the passive layer does not itself deform and merely acts as a support component, for most actuator designs the passive layer itself expands, contracts, bends or deforms elastically in response to the deformation of the active layer For example, for a longitudinal actuator the passive component can be used to amplify the strain rate of the active component and. for a bending mode actuator consisting of a unimorph, the passive component's characteristics heavily influence the actuator performance. For such actuators the passive layer material and design, herein referred to as a "deforming passive component", is integral to the actuator performance and modifying it or adding to its mass will impact the device performance.

For all such actuators a range of factors impact their performance By performance, we mean their ability to cause the membrane to produce droplets whilst maximising the efficiency, minimising the size and minimising the cost of the overall system. Efficiency is here defined as the ideal energy required to produce the droplets divided by the energy into the system.

In relation to the actuator, particular features that improve performance are reducing actuator mass, reducing internal energy dissipation and reducing energy transmitted to components, other than the perforate membrane as described in the following paragraphs.

Reducing actuator mass in general increases performance. This is because any mass needs to be accelerated requiring a force to be applied and increasing the stored energy. For a given quality factor (Q-factor), this leads to additional energy dissipation per vibration cycle. Other disadvantages of increasing actuator mass are an increase in actuator starting and stopping time and either increased complexity, increased cost or reduced efficiency of any drive circuitry, or a combination thereof.

Reducing internal energy absorption of the actuator (i.e. increasing its Q-factor) is important as this energy is dissipated as heat rather than being delivered to the membrane Deformation of both the active and passive components of the actuator leads to thermal heating as does deformation of any bonding materials. For example, for o bonding mode actuator the active and passive components are usually bonded together using an adhesive. Keeping this adhesive layer thin and rigid helps to avoid it absorbing excessive energy.

Reducing energy transmission from the actuator to parts other than the perforate membrane improves performance. This includes the liquid to be delivered as droplets (except in the vicinity of the membrane perforations). In general this can be accomplished by minimising the vibrational amplitude of the actuator (whilst maximising the vibrational amplitude of the membrane). Further, actuators usually need to be mounted to a support structure in order to operate as part of a device and for liquid to be reliably delivered to the perforate membrane. The design and implementation of this mounting can have a significant impact on the actuator performance and the amount of energy transmitted to the perforate membrane. A range of support structures are known in the art for different actuator types (long thin fingers and soft support rings being two such approaches) but in general they try to reduce the transmission of vibrational energy from the actuator to the mount. This can be more easily achieved when the mount does not need to support any large reaction forces that result from forces being applied to the actuator or perforate membrane elsewhere.

Generally Applicable Membrane Design and Actuator Attachment

To transmit energy efficiently from the actuator to the membrane requires careful design of the two components and their interaction. Aside from ensuring the components vibrate at the appropriate frequency and with the appropriate mode shape, a range of generally applicable features are required to deliver maximum membrane velocity for minimum energy consumption. This list of features is similar to what makes a good actuator but with some differences.

Firstly, the mass of the membrane should preferably be minimised especially any mass that does not stiffen the membrane. Minimising its mass reduces the force that must be supplied to it by the actuator reducing losses in that component. Any mass increases increase the required force that needs to be supplied requiring a larger, less efficient actuator.

Secondly, unless the membrane is separately supported (leading to reduced efficiency), the interface between the actuator and the membrane needs to transmit a periodic force oscillating about a mean of zero if gravity is neglected (i.e. the interface must support an instantaneous forces being applied in more than one direction). This may be push/pull, clockwise/anticlockwise torque, or similar.

Thirdly the energy absorbed in the interface between the actuator and the membrane should preferably be minimised. For devices which do not require the separation of the perforate membrane this can be achieved by several methods well known in the art. These include adhesive bonding, welding, brazing and soldering amongst others. All such means add minimal, if any, mass to the device, generally absorb little energy and do not reduce the amplitude of vibrations. They achieve these features by creating a very thin rigid bond directly between the two components. Bolting, clamping or screwing together the components is also used but, as previously discussed, this increases mass and can also impact the vibrational characteristics of the device.

Finally, energy transmitted to the liquid that does not go into the formation of droplets should preferably be minimised. This can be achieved by minimising any area of the membrane that is not perforate (i.e. by minimising areas of vibration that are liquid contacting but are not delivering droplets). Energy transmission to the liquid can also be reduced by using soft wicks or other similar means to deliver liquid rather than contacting the membrane with bulk liquid.

Figure 4:
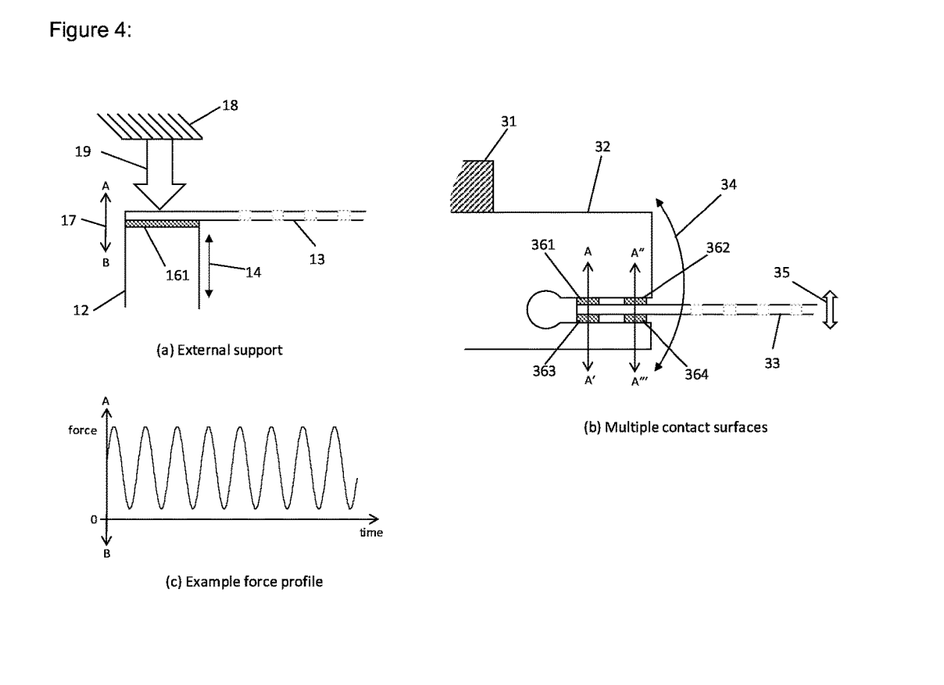

To summarise, any separable membrane design would ideally allow efficient transmission of energy from the actuator to the membrane in the form of an oscillating force about a mean of zero without absorbing energy. It would ideally minimise any mass increase of both the actuator and the membrane It would ideally minimise any increased damping in the actuator. It would ideally minimise the energy transmitted by the actuator to elements other than the membrane (e.g. mount). It would ideally avoid transmitting energy to the liquid to be delivered.

BRIEF DESCRIPTION OF THE DRAWINGS

Aspects of the Invention

Magnetic connection between the actuator and membrane has the ability to meet all of these preferred requirements. A range of aspects of the invention are now disclosed with reference to the following figures:

FIG. 1 summarises a range of actuator types and their interface to the perforate membrane for current, non-separable constructions.

FIG. 2 is a detail view of the actuator to membrane interface showing the forces that need to be transmitted.

FIG. 3 is the output of a finite element model predicting the magnitude of the forces transmitted from the actuator to the membrane for a bending mode actuator.

FIG. 4 illustrates embodiments in which each bond only needs to transmit a unidirectional force.

FIG. 5 is a preferred embodiment of the invention in which the passive component of the actuator is a permanent magnet and the membrane is made of a ferromagnetic material.

FIG. 6 shows the typical force magnitudes that can be transmitted for various magnetic connection designs.

FIG. 7 presents a range of variants on the magnetic substrate bending mode actuator, including variants that make use of a support ring.

FIG. 8 presents a variant on the magnetic substrate bending mode actuator in which a support ring forms part of a dose capsule and is located at a nodal position.

FIG. 9 shows two example actuator and membrane mounting mechanisms in which the actuator and membrane connection does not involve direct contact.

FIG. 10 shows two example actuator and membrane mounting mechanisms designed to minimise overall damping.

FIG. 11 shows example embodiments of liquid containing capsules in which the liquid is brought into contact with the perforate membrane shortly before delivery.

FIG. 12 shows alternative capsule designs to that shown in FIG. 8 which contain features to increase the spray orientation of the apparatus.

FIG. 13 is an embodiment of the invention in which the membrane completes the magnetic circuit.

DETAILED DESCRIPTION OF THE INVENTION

FIG. 1(*a*) shows an axi-symmetric droplet production apparatus known in the art of the longitudinal type (1). The actuator consists of an active component (11) bonded to a deforming passive component (12) designed such that at resonance the passive component amplifies the strain of the active component. A perforate membrane (13) is bonded to the actuator and the device has an overall axis of symmetry (10). Expansion and contraction of the actuator (14) leads to amplified motion (15) of the perforate membrane in a generally parallel direction. The membrane itself may all vibrate in phase, have one wavelength of motion across its radius (i.e. the central region may be out of phase with the periphery), or more than one wavelength of motion, depending on the design. FIG. 2(*a*) shows the detail of the actuator to membrane interface for this apparatus. The membrane is permanently attached to the actuator through a means such as adhesive bonding, laser welding, brazing, soldering or similar (16). This attachment mechanism must transmit a time varying force (17) across the interface with the force primarily normal to the bonding surface in directions A and B. Such a force, be way of an example, is sketched in FIG. 2(*d*). When the force is in direction A the bond (16) is in compression and when the force is in direction B the bond is in tension.

FIG. 1(*b*) shows another axi-symmetric droplet production apparatus but of the breathing type (2). Again the actuator consists of an active (21) and passive (22) component but in this instance planar actuator motion (24) leads to vibration of the membrane (23) in a direction normal to the actuator motion (25). The bond interface is shown in FIG. 2(*b*). For this type of actuator the bond (26) must primarily support the transmission of a shearing force (27) in a time varying radially inwards and then radially outwards direction.

A third type of device (3) to which this invention is applicable is shown in FIG. 1(*c*). This device uses a unimorph actuator comprising an active (31) and a deforming passive (32) layer that operates in bending (34). This bending motion is connected to the membrane (33) and drives the membrane to vibrate in a direction (35) normal to the unimorph neutral plane. The bond detail is shown in FIG. 2(*c*) and in this case the bond (36) must transmit a time varying torque (37*a*) and normal force (37*b*) from the actuator to the membrane. The relative intensities and phases of these two bulk forces will be design dependant but the result is that the bond must support radially and time varying shear, compression and tension across its surface. FIG. 3 shows this in more detail for a specific actuator design based on the results of Finite Element Modelling. Whilst this model only partially captures the physics of the motion (for example it assumes small deflections), it does show the complexity of the forces transmitted, in FIG. 3(*a*) the time varying normal and shear forces at the inner radius of the actuator passive component are plotted over a single time cycle showing both normal and shearing forces, both in two directions must be transmitted to the perforate membrane. FIG. 3(*b*) shows how the peak normal and shear forces that must be transmitted vary across the bond width. Peak normal force is predicted to be roughly uniform across the bond width except for a peak very close to the inner radius.

For all three bonds (16, 26 and 36) described above, the forces that must be supported are bi-directional, it is possible to enable the bond or bonds between the actuator and membrane to only support a unidirectional force but this requires the application of an external support or the use of multiple bonding (or contact) surfaces. This is illustrated in FIG. 4. In FIG. 4(a) a force (19) is applied from an external support (18) to compress the membrane to actuator bond resulting in the bond (161) only having to support a time varying compressive force (as illustrated in FIG. 4(c)). This has the advantage in that the bond could be achieved simply by pushing the two components together but results in reduced efficiency as vibrational energy will be dissipated in the force application mechanism (19) and the actuator mount.

Another means of enabling the actuator to membrane bonds to only need to support unidirectional forces is through the use of more than one bond surface as illustrated in FIG. 4(b). This example is of a bending mode device in which the time varying force and moment is transferred through four bond Surfaces (361 to 364). Each of these bonds only has to primarily support a time varying compressive force (a small shear force will also need to be supported). This example covers screw threads and bayonet type fittings. It should also be noted that bonds 361 and 362 can be merged as can bonds 363 and 364 resulting in a radially varying force across their width. Key disadvantages of such approaches are increased attachment and detachment complexity, increased manufacturing complexity and increased thickness.

It should be noted that the discussion relating to the above examples is broadly applicable to other actuator designs. Further, whilst the examples generally illustrate vibration at the actuators first resonant frequency of the applicable mode (i.e. lowest frequency bending mode), the discussion and this invention is equally applicable to higher order mode actuation.

Bidirectional forces and torques between the actuator and membrane can be created directly through the use of magnetism. This is advantageous over other temporary bonding mechanisms (such as using a biasing spring to push them together) as it negates the need for a $2^{nd}$ force application mechanism (such as a biasing spring or $2^{nd}$ mechanical interface) as discussed above.

Figure 1:
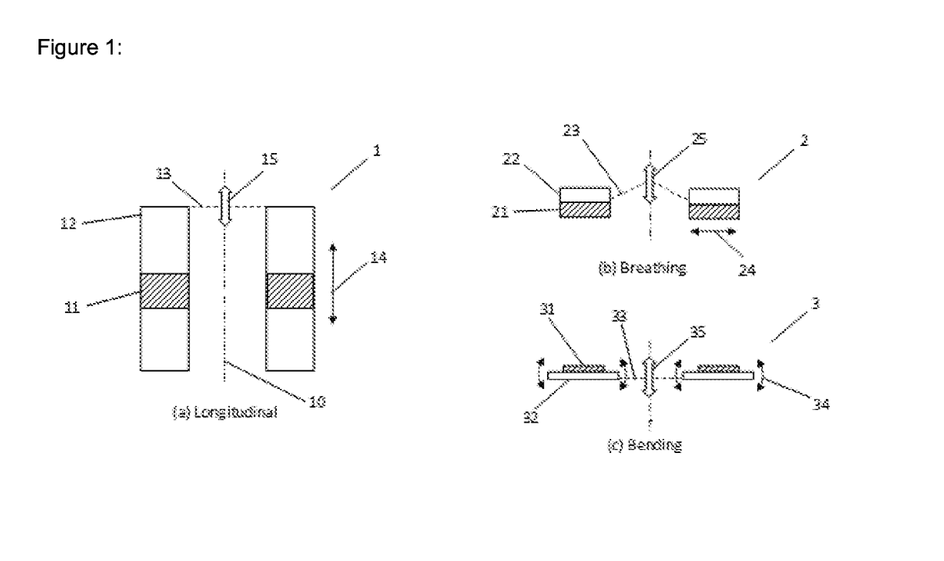
Figure 2:
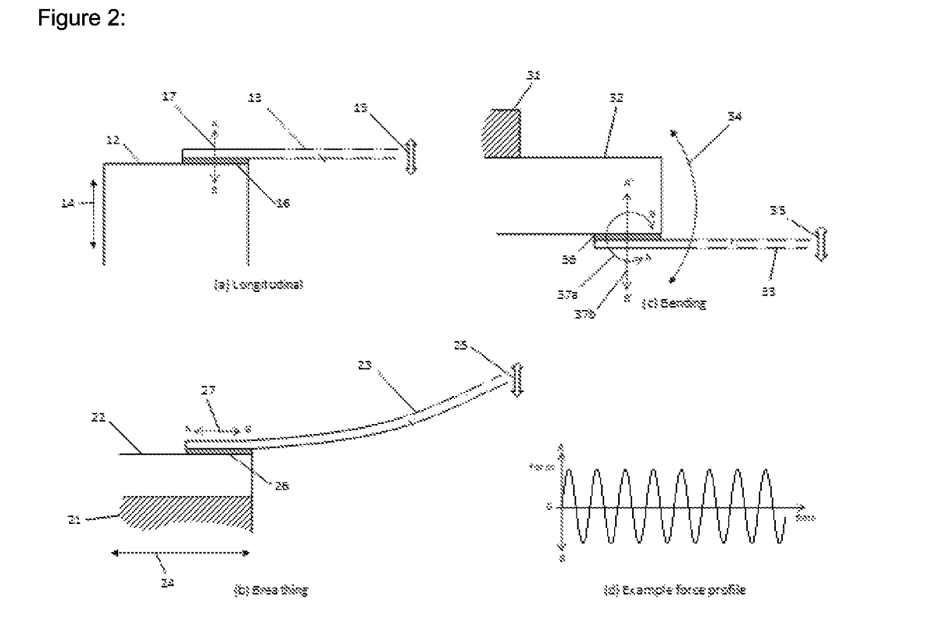
Figure 3:
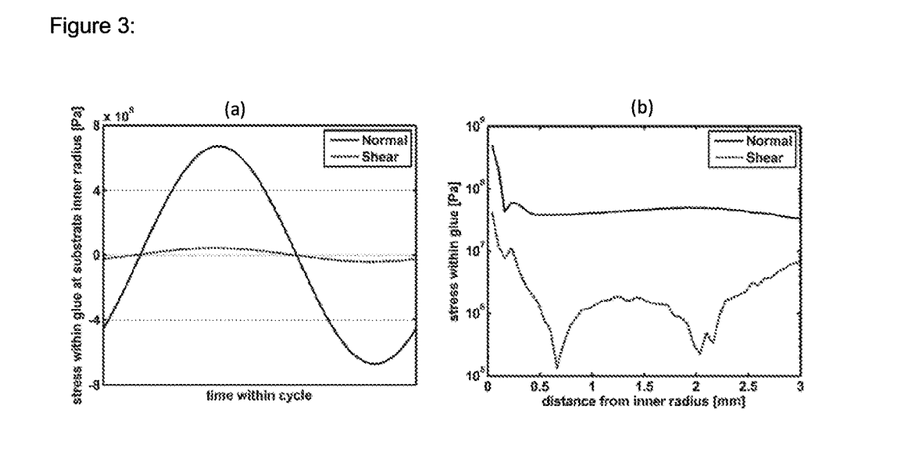
Figure 5:
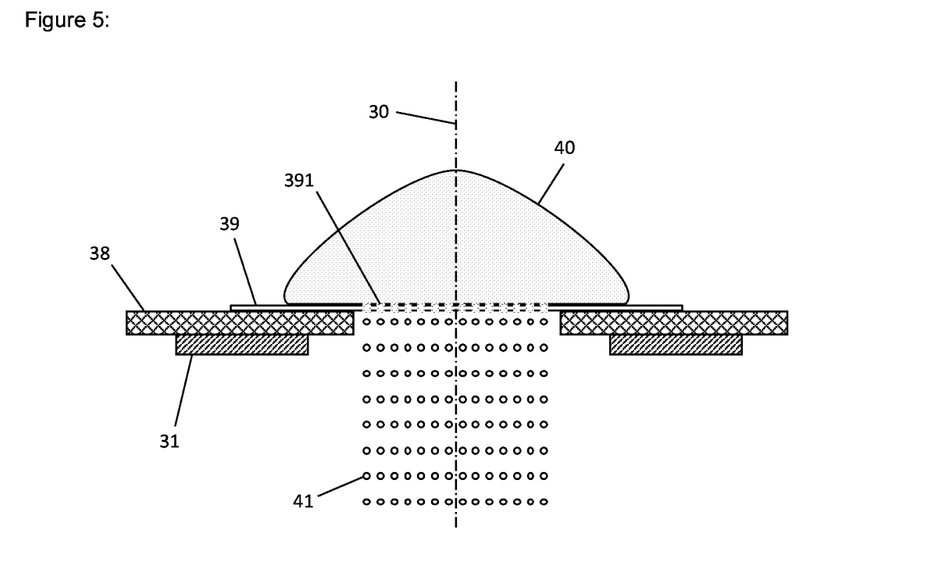

In a preferred embodiment of the invention, the magnetic force is created through the use of a permanent magnet forming part of the actuator. For actuators with deforming passive components, then in a preferred embodiment the magnet forms part of this deforming passive component. FIG. 5 shows one preferred embodiment of the invention. In this embodiment, a thin disk unimorph actuator similar to that shown in FIG. 1(c) acts in bending mode driven by a piezoceramic component, 31. The use of a bending mode actuator is preferred due to its compact size, low mass and high efficiency. The deforming passive component in FIG. 1(c) (32) has been replaced by a permanent magnet (38), in this case a nickel plated NeFeB rare earth magnet which is axially magnetised (i.e. its poles are at the two surfaces that form planes normal to the axis of symmetry). By replacing the deforming passive component (which is typically made of steel, copper, brass or aluminium) rather than adding a new component, no mass has been added to the actuator. In this example, the actuator is of unimorph type, a preferred embodiment. The perforate membrane is preferably made from a ferromagnetic material. In this embodiment, the perforate membrane (39) is made from 50 µm thick Martensitic Stainless Steel stamped sheet in which tapered perforations (or nozzles, 391) have been made through laser drilling. A bulk of liquid (40) sits on one side of the membrane either constrained in a reservoir/capsule or in droplet form and, during actuation, is delivered through the tapered nozzles (from the more open to the more closed side) as droplets (41).

In this embodiment with a 100 µl droplet of liquid placed on the membrane, flow rates of over 9 µl/s have been observed through a membrane with 3289 nozzles in which the mass mean aerodynamic diameter was ~4.5 µm, i.e. ideal for drug nebulisation. Such results are purely included by way of an example and should not be construed as a limit to the capabilities of the invention. Such a device with a single nozzle could be used in a drop on-demand manner for accurate dispensing of fluid or printing for example.

Discussing the actuator, powerful permanent magnets are preferred and therefore Neodymium Iron Boron (NeFeB) rare-earth magnets are ideal. These can be readily manufactured into disks although, unless a poor yield and higher cost can be accepted, at present thickness of less than 0.4 mm are hard to make. This is thicker than the deforming passive component of some current bending mode actuators (for example that found in the eFlow made by Pari GmbH) and hence basing the design on actuators with a thicker passive component is desirable. In the example above, the deforming passive component is 0.5 mm thick. Whilst this can be increased further it stiffens the structure reducing resonant vibration amplitude for a given active component. Therefore a passive component thickness between 0.4 mm and 1.0 mm is considered ideal for such a device although the invention is still applicable to a wider range of thicknesses.

Discussing the membrane, being generally constructed of a thin material of 150 μm thickness or less, preferably 100 μm or less, connection force is limited by magnetic saturation of the material (rather than by permissivity for example). As such relatively high saturation ferromagnetic components (ideally those with a saturation induction of greater than 1.6 tesla) are preferred. Examples of such preferred materials that are also suitable for laser drilling include Martensitic and Ferritic Stainless Steel and Permendur. Ferromagnetic materials with tower saturation levels such as Mumetal and Nickel in general deliver reduced performance. However, Nickel has the advantages of being electroformable (a common means of manufacturing a perforate membrane) and hence may be a preferred membrane material in some embodiments.

FIG. 6 shows the relative connection forces between the actuator and membrane for the design presented in FIG. 5 for various membrane materials. Unless otherwise stated, all embodiments in FIG. 6 have the following geometrical features; inner radius of actuator passive component of 4 mm, outer radius of actuator passive component of 11.4 mm, thickness of actuator passive component of 0.5 mm, outer radius of perforate membrane of 8 mm, thickness of perforate membrane of 50 μm. For Embodiments E to M discussed below, a support ring is also used with the following dimensions: inner radius of 4 mm, outer radius of 6.5 mm, thickness of 0.5 mm.

Referring to FIG. 6. Embodiment A is the embodiment described above which delivered a 9 μl/s spray rate and the estimated magnetic attraction force for this embodiment is 0.5N. Embodiment B and C show the relative force changes when different mesh materials are used. Whilst axial magnetisation has been shown to deliver good droplet generation performance, connection force can he enhanced through the use of radial magnetisation in which one pole is located at the inner radius of the deforming passive component and the other pole at the outer radius. Therefore in a preferred embodiment of the invention the actuator is formed from a generally axisymmetric ring and the magnetic polarisation of the permanent magnet part is radial and normal to the ring axis of rotational symmetry. Manufacture of such parts is more challenging as a strong radial magnetic force needs to be applied during magnet manufacture requiring custom tooling and hence may not always be preferable. Therefore, in some instances, a preferred embodiment of the invention has the actuator formed of a generally axisymmetric ring and the magnetic polarisation of the permanent magnet part is parallel to the ring axis of rotational symmetry. For the embodiment considered in FIG. 5 and FIG. 6, using radial rather than axial magnetisation is expected to deliver a four-fold increase in connection force (Embodiment D in FIG. 6). Such an approach may also be beneficial to linear devices in which the perforate membrane and actuator take the approximate shape of an extruded two dimensional structure in which the extrusion length of the perforated section of the perforate membrane is greater than its width. For such linear devices, the preferred magnetisation direction would be substantially normal to the droplet generation direction.

If additional connection force is required (for example to enable the device to be driven with more power so that a more viscous formulation can be dispensed) or if a non ferromagnetic membrane has to be used for other reasons then a permanent magnet or ferromagnetic support structure either bonded to the membrane or clamping the membrane to the actuator can be used in addition to or instead of using a ferromagnetic membrane material. In one preferred embodiment the permanent magnet of ferromagnetic support structure, in use, damps the perforate membrane to the actuator. This arrangement enables the support structure to be reused if required rather than requiring one support structure for each perforate membrane. In another preferred embodiment, the permanent magnet or ferromagnetic support structure is permanently bonded to the perforate membrane. This arrangement enables, but does not necessitate, the support structure bong between the actuator and the perforate membrane which may be beneficial in some cases.

Figure 6:
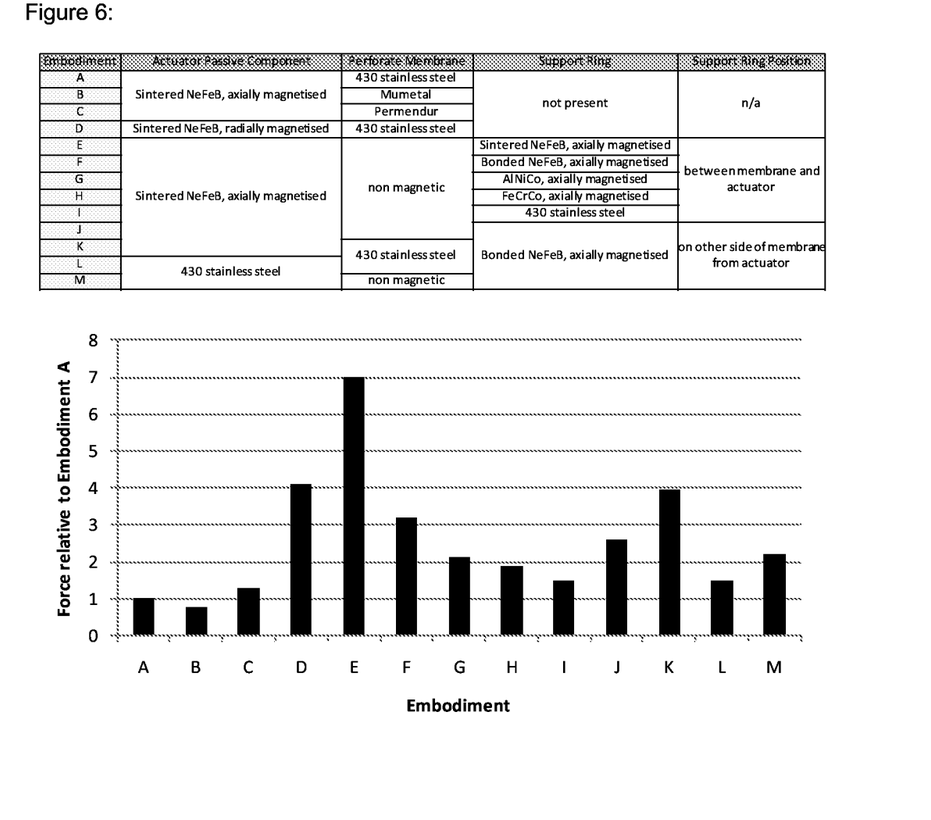

It should be noted that here the term 'support' primarily refers to the fact that the structure supports the connection of the energy transmission from actuator to membrane. Such structures can also be used to provide mechanical support to the membrane when not in use or when not attached to the actuator. Whilst this necessarily increases the mass of the device, this increase can be minimal. FIG. 6 Embodiments E to M show the connection forces created through the use of various 2.5 mm×0.5 mm cross section support rings that have an internal diameter that matches the actuator internal diameter. Use of soft ferromagnetic material (such as 430 series stainless steel) can provide a small connection force increase relative to no such support ring but use of a hard magnetic ring can deliver increased force. As an alternative, the actuator passive component can be made from a soft ferromagnetic material and the support ring a hard ferromagnetic material.

Whilst with one nard and one soft magnetic material only an attractive force can be created, with two hard magnetic materials then torque can also be directly created. This can be used to aid the connection of the components and can also be used to help self-centre the membrane to the actuator. To further aid the transmission of forces beyond those normal to the contact surface (and also applicable to cases when one soft and one hard magnetic material is used), surface features of the actuator or membrane contact area can be used in which the surface features leads to an increase in the static coefficient of friction and/or aids alignment of the membrane to the actuator. Example features include ridges, troughs, upstands and holes. Such features can also aid in the alignment of the actuator to the perforate membrane. Therefore, in a preferred embodiment, the perforate membrane surface that contacts the actuator has mechanical features extending in a direction normal to the contact surface that interface with features of the actuator. Texturing, roughening, and the addition of a non-slip coatings may also be of benefit.

Figure 7:
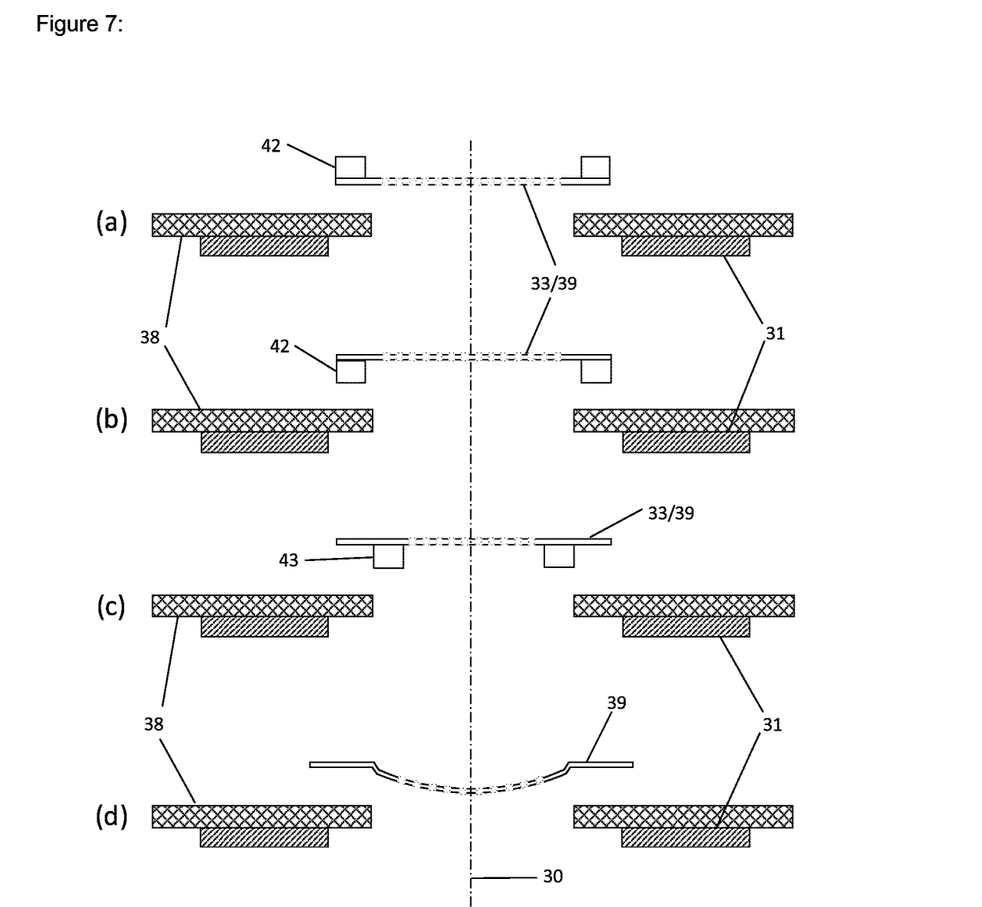

FIG. 7 provides example embodiments of the use of a ferromagnetic support structure In FIG. 7(a) the structure (42) may or may not be permanently bonded to the membrane (33 or 39) and clamps the membrane to the actuator. In FIGS. 7(b) and 7(c) the support structure is permanently bonded to the membrane. FIG. 7(c) has the added benefit of being able to use the support structure (43) for alignment. Such alignment could be achieved by other moans, one example of which is shown in FIG. 7(d). Here the perforate membrane is domed after laser drilling to increase stiffness with the outer features of the dome used for alignment purposes.

Figure 8:
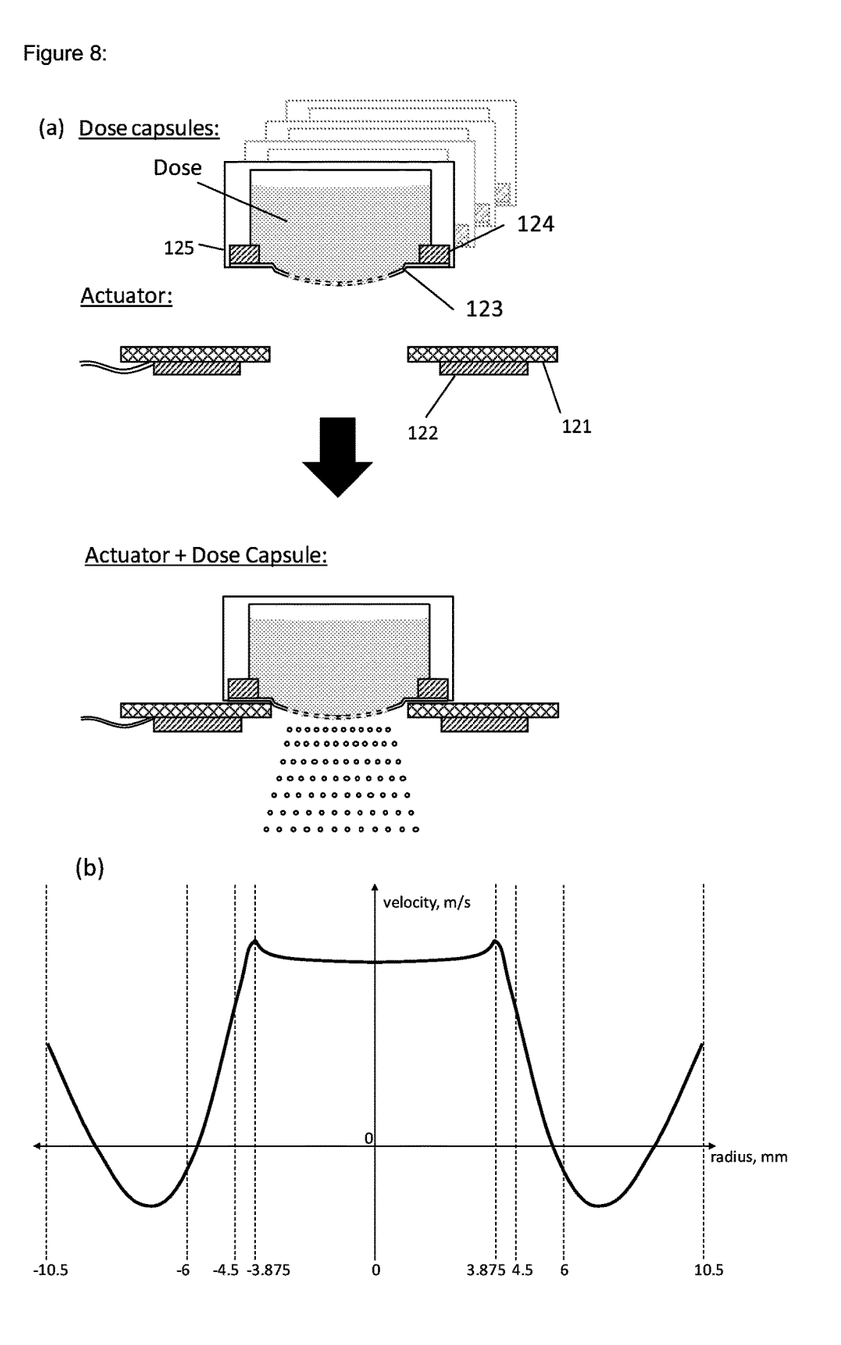

FIG. 8(a) presents a preferred embodiment that makes use of e hard magnetic support ring (124) to deliver enhanced performance. In this embodiment, the deforming passive component of the bending-mode actuator (121) is made from a magnet, typically made of Zinc coated NeFeB, axially magnetised with an internal diameter of 7.75 mm. an outer diameter of 21 mm and is nominally 0.5 mm thick It is bonded to a PZT disc (122) of the type made by Pari GmbH of PIC151 material with internal diameter 12 mm, outer diameter 19 mm and thickness of 0.20 mm. Zinc coating of the magnet was used to improve bonding between the two components. Other coating materials may also enable improved bonding including nickel, epoxy and gold. The capsule consists of a 100 μm thick 430 stainless steel disc (123) that has been laser drilled to create ~3000 perforations and then domed with an approximate dome radius of 10 mm and the dome extending out to a diameter just less than the internal diameter of the actuator This perforate membrane has been bonded to a magnet support ring (124), typically made of NeFeB, axially magnetised (and orientated such that it will be attracted to the deforming passive component when located) with internal diameter 9 mm, outer diameter 12 mm and thickness of 1.5 mm. Optionally, a thin plastic cover (125) was attached to this support ring to create a closed volume in which the liquid to be dispensed was housed and a pressure difference relative to atmospheric pressure could be applied (with a slight reduced pressure known to improve performance for such devices).

This preferred embodiment benefits from excellent repeatability and performance with easy location of the capsule relative to the actuator The apparatus operates with the perforate region of the membrane alt in phase which minimises the impact of any manufacturing variation as vibration wavelengths are maximised. Using saline solution delivery rates m excess of 20 μl/s were demonstrated with droplet size (D(4,3)) of approximately 4.5 μm and delivery rates in excess of 140 μl/s were demonstrated with droplet size (D(4.3)) of approximately 9 μm One preferred feature of this embodiment that is thought to be beneficial is the placement of the support ring at, or close to, a nodal position of the apparatus. By this we mean that the support ring is located such that, in use, a nodal point of the actuator is located between, or within 0.5 mm of, the support ring internal and outer diameters. This is illustrated by FIG. 8(b) which shows representative motion of the embodiment described above at the point of peak membrane velocity as measured using a laser scanning vibrometer through scanning of the front (droplet ejection side) surface of the device at resonance. Between 0 and 3.875 mm radii the line shows the velocity of the perforate membrane and between 3.875 mm and 10.5 mm radii the fine shows the velocity of actuator. It should be noted that this line shows representative motion only as in reality the motion is not fully axisymmetric. Referring to the figure, the actuator nodal positions are at approximately 5.7 mm and 9.0 mm radii and the first of those is between the inner and outer radii of the support ring. This positioning means that the movement of the support ring is minimised reducing the required energy transfer from the actuator and improving performance. Positioning the walls of the capsule or reservoir such that they contact the perforate membrane and/or actuator at or close to the nodal position of the actuator when in use is also thought to be beneficial. This applies whether or not a support ring is utilised as it minimises the movement of said walls and hence reduces the amount of energy that needs to be transferred from the actuator. Such positioning can also be used for the mounting of the apparatus (actuator plus capsule/reservoir) to the device itself. This may enable the actuator to support structure mount to be removed or minimised (i.e. the actuator can be structurally mounted to the rest of the device via the capsule/reservoir) which may be beneficial for some embodiments.

Figure 9:
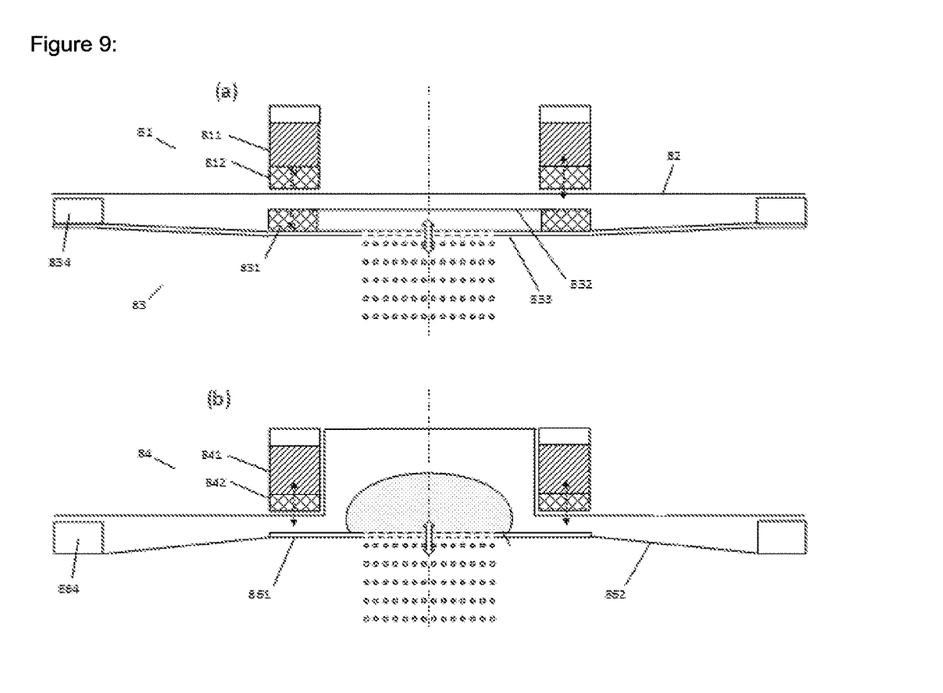

In many instances, and as described in the embodiments above, it is expected that it will be preferable for the actuator and membrane to be in direct physical contact. In these cases the magnetic force will preferably be attractive. This invention can also though be embodied in forms in which the membrane and actuator are not in direct physical contact. This may be by separating the two parts with a thin passive layer for hygienic or aesthetic purposes for example. In addition, by avoiding physical contact it is possible to amplify the displacement such that the whole of the perforate membrane is displaced to a greater extent than any part of the actuator. This is beneficial as it can increase efficiency and require less actuator motion for a given amount of membrane motion. Therefore in one preferred embodiment of the invention the actuator and membrane are not in direct physical contact during operation and are configured such that the amplitude of the perforate membrane motion adjacent to the actuator is greater than that of the actuator itself. Means of achieving this amplification including attaching the membrane to a structure that is designed to mechanically resonate at the frequency of actuator oscillation. This structure could consist of an annular drum-skin or skirt for example (which may be an extension of the membrane itself). Alternatively the resonant structure could be a spring again designee to vibrate at or close to the actuator frequency. FIG. 9 presents two example embodiments.

In FIG. 9(a), the actuator (81) is of the longitudinal type consisting of active component (811) and passive component (812) in which the passive component is a permanent magnet axially polled as indicated in the figure. The actuator is located behind a fixed wall (82). The fluid to be dispensed is contained in a subassembly (83) consisting of a permanent magnet support ring (831), perforate membrane (833), capsule back surface (832) and mount (834). The mount attaches to the fixed wall in use and, in this embodiment, the support ring is police such that it is repelled by the actuator when mounted. The perforate membrane is extended between the support ring and mount such that it holds the subassembly together, keeps the support ring close to the actuator passive component and flexes in a resonant manner when actuated. The liquid is contained within the surfaces comprised of the perforate membrane, the support ring and the back surface In FIG. 9(b) another example embodiment is shown. The actuator (84) is of similar type to that shown in FIG. 9(a) but here the perforate membrane (861) is made of a soft ferromagnetic material and is attracted to the actuator passive component (842). The mount (864) and skirt (862) hold the perforate membrane away from the actuator. In this embodiment the skirt is a separate component from the perforate membrane connected to it and designed to enable motion amplification between the actuator and membrane with minimal energy dissipation. It should be noted that FIG. 9 presents example embodiments in which the actuator and membrane are not in direct physical contact and several alternative embodiments will be obvious to someone with knowledge in the an based on this specification.

Figure 10:
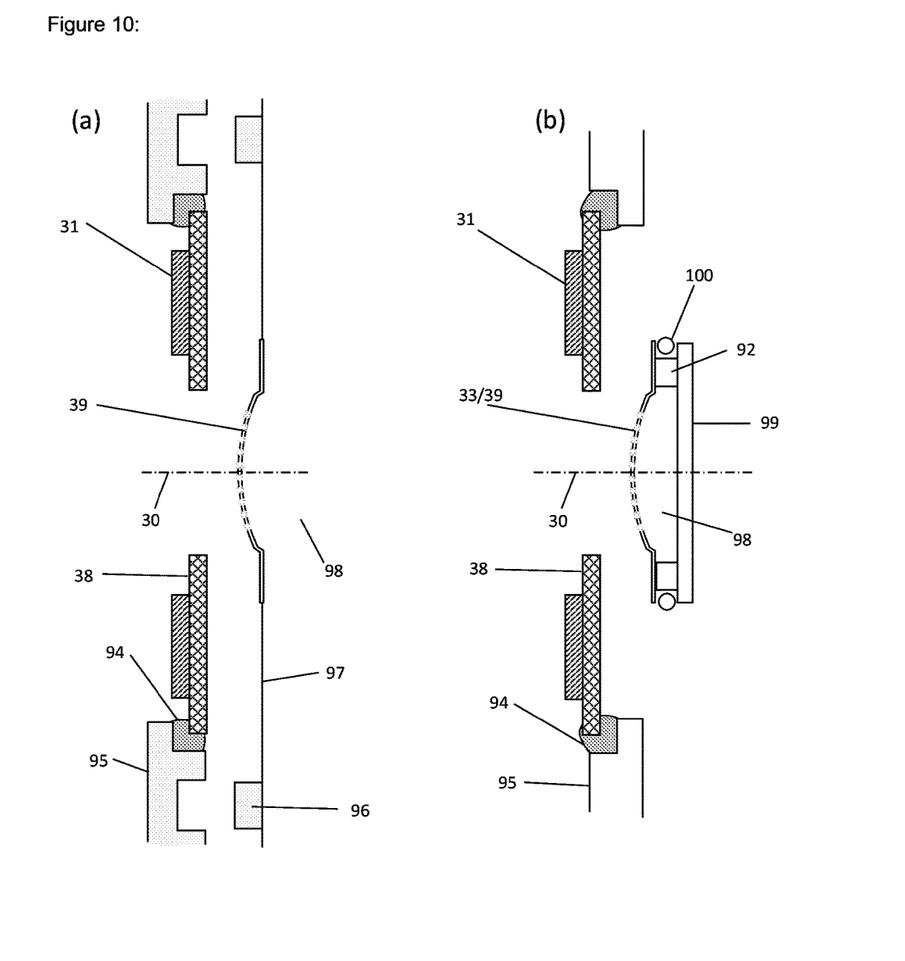

Whilst the perforate membrane may be brought into contact with the actuator independently from the introduction of the liquid to be dispensed, in many applications it is beneficial for the membrane and liquid to be stored and brought to the actuator together. Therefore in a preferred embodiment, the perforate membrane is permanently attached to the liquid containing reservoir. FIG. 10(a) shows one such embodiment, ideally suited for low cost consumer applications, in which the membrane (39) is bonded to a flexible support structure (97) that forms part of the liquid containment reservoir (98). This flexible support structure can be a dispensed silicone or low shore hardness elastomeric compound. Alternatively, and as shown in FIG. 10(a) it can be a flexible bag made of one or more thin film layers. This flexible support is not just applicable to cases in which the membrane is supplied with the fluid. Therefore, in a preferred embodiment, the perforate membrane is supported when not in contact with the actuator by means of a flexible support. Referring to the example embodiment in FIG. 10(a), such a bag may form just a part or the majority of the liquid containment structure, location features (96) can be used to aid initial membrane to actuator alignment. This reservoir (98) consists of all liquid contacting components and may be user replaceable. The actuator comprising active (31) and deforming passive (38) components is here bonded to a rigid support structure (95) on the master device using a tow shore hardness silicone (94). Other low damping supports such as thin long fingers can be used for this connection as the interface does not need to be liquid tight.

FIG. 10(b) shows an alternative embodiment more suited for capsule based formulation delivery. In this embodiment each capsule consists of a perforate membrane (33 or 39), a ferromagnetic support ring (92) which also forms part of the capsule liquid containment structure, a preferred embodiment, and a backing (99) that completes the reservoir (98). Such a backing may be rigid or flexible. When not attached to the actuator the capsule is loosely supported by an outer structure (100) that could, for example, be part of a tape structure holding many capsules. This structure is used to move the capsule to the vicinity of the actuator at which point it becomes aligned and connected though the magnetic forces pulling the capsule into the actuation position. When attached to the actuator there is little if any contact with the support structure (100) minimising energy loss through damping.

Figure 11:
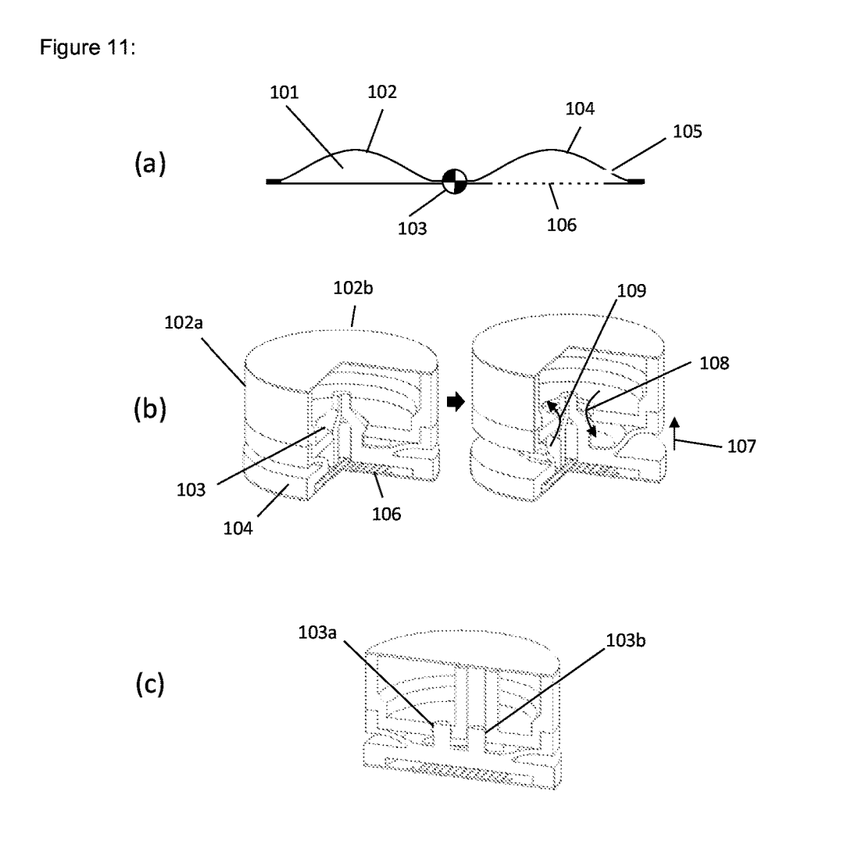

Other features, generally applicable to a broad range of perforate membrane droplet generation apparatus, can be added to this capsule to aid sterility and reduce liquid toss through evaporation for example. Such features include a peelable cover over the perforate membrane and an internal valve that only introduces liquid to the membrane shortly before use. Example embodiments of such an internal valve are shown in FIG. 11. In the embodiment examples in this figure there is provided, for use in a liquid droplet generation apparatus, a perforate membrane packaged together with the liquid to be dispensed through the perforate membrane, in which the liquid is stored in a substantially fluid-tight compartment, in which the stored liquid is brought into contact with one side of the membrane prior to droplet generation from the other side of the membrane, in which said droplet generation is caused by the vibration of the membrane.

In FIG. 11(a), a pouch (102) containing the liquid to be delivered (101) is separated from a similar volume empty pouch (104) in which the perforate membrane (106) makes up one side. On the application of pressure to the liquid containing pouch the valve (103) which was fluid tight opens allowing liquid to flood behind the mesh with air escaping through a vent (105).

The action that results in liquid being brought into contact with one side of the perforate membrane preferably also results in the liquid being at a pressure slightly below atmosphere pressure once in contact as this is known to enhance droplet generation. Several means of achieving this are possible. The capsule can be designed to increase in volume. One or more surfaces of the capsule can be mechanically biased or sprung such that they exert a force on the liquid. Some of the liquid, or a gas stored with the liquid, can be extracted once the liquid is in contact with them membrane. A gas stored with the liquid could be cooled. Further the capsule structure could have two stable states, one with the liquid in a fluid tight compartment and one, with increased capsule volume, with a fluid path created between the compartment and the perforate membrane. Examples of a capsule whose volume increases as part of the action that brings the liquid into contact with the perforate membrane are shown in FIG. 11(b) and FIG. 11(c) in which the valve opening motion is substantially normal to the perforate membrane surface, a preferred embodiment. In FIG. 11(b) the sterile liquid containing chamber is made up of a moulded component (102a) and lid (102b) in which the lid is added after the liquid is dosed into the capsule. The lid may be foil or moulded plastic for example and could be adhesively bonded, heat staked or ultrasonically welded to the moulded component (102a). The valve (103) forms part of the empty pouch component (104) to which the perforate membrane (106) is connected. On movement of the liquid containing compartment away from the mesh surface (107), the valve opens allowing liquid to come into contact with the perforate membrane (108) and air to replace it (109). As the overall volume of the two chambers (102 and 104) increases, air will enter the chambers through the perforate membrane. So long as liquid comes into contact with all the membrane perforations before the capsule motion (107) has completed then fluid pinning on the perforations will limit this air entry resulting in the liquid being at a pressure below that of the surrounding atmosphere. This is known to enhance droplet production performance. Ensuring liquid is in contact with the membrane perforations before the motion (and corresponding volume increase) is complete cart be achieved through slow or two stage opening of the valve, careful valve design or through the use of more than one valve as shown in FIG. 11(c). Here valve 103b enables air to replace liquid in the sterile capsule whilst valve 103a enables liquid to rapidly How into contact with the perforate membrane.

Figure 12:
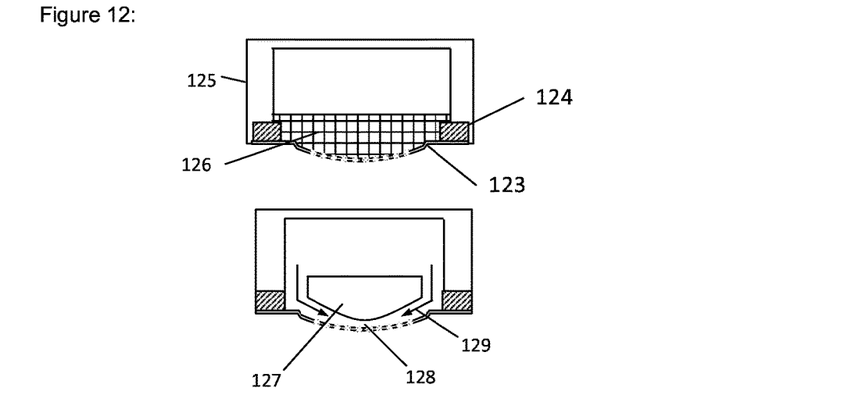

Other features, generally applicable to a broad range of perforate membrane droplet generation apparatus, can be added to this capsule to increase orientation independence. For example, as shown in FIG. 12, a porous material (126) such as an open cell foam of a wick can be placed in contact with the liquid side of the perforate membrane. This will assist in maintaining liquid contact with the membrane as the capsule empties. Other features that will be beneficial in certain embodiments include the use of a plate or similar structure (127) located close to and substantially parallel to the perforate membrane surface and shaped so that surface tension draws liquid towards the perforate membrane centre as fluid is dispensed (129). For such structures the minimum distance between membrane and structure (128) surfaces should be 2.0 mm or less with smaller values preferable especially for low surface tension liquids.

Whilst the features and embodiments discussed above have been primarily related to axisymmetric bending mode devices to which they are exceptionally beneficial, they also have wide applicability in relation to other actuator types including those of radial and longitudinal type. They are also applicable to linear style and other non-axisymmetric designs.

Figure 13:
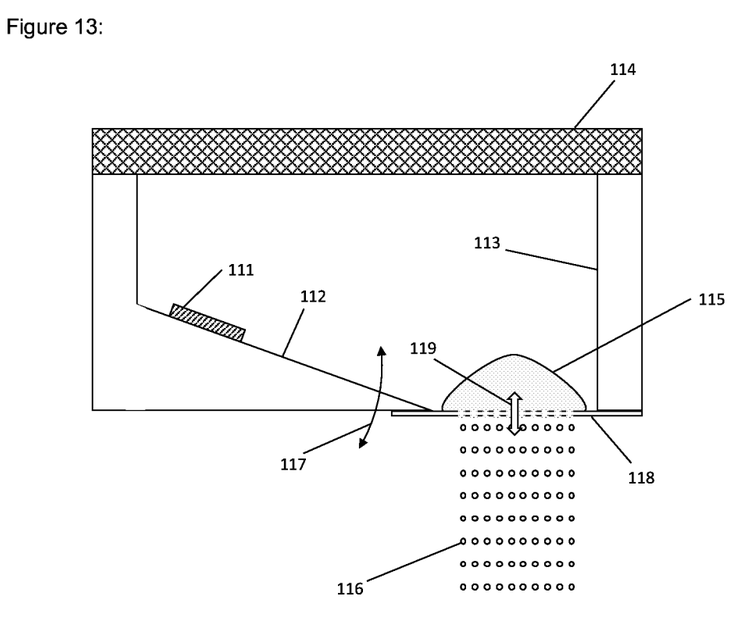

For linear actuators, an alternative means of utilising a magnetic connection force is disclosed in FIG. 13. Here the membrane (118) completes the magnetic circuit enhancing the attractive force that would otherwise be present. The actuator is of a wedge type comprising active (111) and deforming passive (112) component in which the wedge amplifies the vibrating motion. The membrane is connected to the thick end of the wedge and connected across to a non moving support structure (113). This non moving structure can be replaced with an active and passive component creating an axis of symmetry through the centre of the membrane for some embodiments. The deforming passive component (112) and support structure (113) are formed of a suitable ferromagnetic material and connected to a substantially non-moving permanent magnet (114) in which the magnet is oriented such that one pole is near to the interface to the support structure and the other pole is near to the passive component. The advantage of this embodiment is that by using a wedge design the permanent magnet is not vibrated.

The invention claimed is:

1. A liquid droplet production apparatus comprising:
a perforate membrane;
a liquid supply configured to supply liquid to one side of the membrane;
an actuator configured to vibrate the membrane, said vibration causing liquid droplets to be ejected from the other side of the membrane;
wherein:
magnetic force is used to connect the actuator to the membrane so that the vibration can be transmitted; and
wherein the perforate membrane is non-removably attached to a liquid containing reservoir.

2. A liquid droplet production apparatus according to claim 1 wherein the magnetic force is created through the use of a permanent magnet comprising part of the actuator.

3. A liquid droplet production apparatus according to claim 2 wherein the magnet is or forms part of a deforming passive component of the actuator.

4. A liquid droplet production apparatus according to claim 1 wherein the actuator is a bending mode actuator.

5. A liquid droplet production apparatus according to claim 1 wherein the magnetisation polarisation is substantially normal to the droplet generation direction.

6. A liquid droplet production apparatus according to claim 1 wherein the actuator and membrane are in direct physical contact during operation and the magnetic force is attractive.

7. A liquid droplet production apparatus according to claim 6 wherein the perforate membrane surface that contacts the actuator has mechanical features extending in a direction normal to the contact surface that interface with features of the actuator.

8. A liquid droplet production apparatus according to claim 1 wherein the actuator and membrane are not in direct physical contact during operation and wherein the apparatus is configured such that the amplitude of the perforate membrane motion adjacent to the actuator is greater than that of the actuator itself.

9. A liquid droplet production apparatus according to claim 1 wherein the perforate membrane is made from a Martensitic Steel, Ferritic Steel or Permendur.

10. A liquid droplet production apparatus according to claim 1 wherein the perforate membrane is made from a ferromagnetic material with saturation induction 1.6 tesla or greater.

11. A liquid droplet production apparatus according to claim 1, wherein the perforate membrane is made from a material with saturation induction of 1.6 tesla or greater.

12. A liquid droplet production apparatus according to claim 1, wherein the perforate membrane is attached to a permanent magnet or ferromagnetic material support structure.

13. A liquid droplet production apparatus according to claim 1 wherein a permanent magnet or ferromagnetic material support structure, in use, clamps the perforate membrane to the actuator.

14. A liquid droplet production apparatus according to claim 13 wherein the support structure is located such that, in use, an actuator node is located between support structure inner and outer limits, or within 0.5 mm of these limits.

15. A liquid droplet production apparatus according to claim 1 wherein, in use, an actuator node is located between inner and outer limits of walls of the liquid containing reservoir, or within 0.5 mm of these limits.

16. A liquid droplet production apparatus according to claim 1 wherein a porous material is in contact with the perforate membrane on the liquid side of the membrane.

17. A liquid droplet production apparatus according to claim 1 wherein a structure is located on the liquid side of the perforate membrane, with the surface of the structure closest to the perforate membrane substantially parallel to the perforate membrane surface, and with a minimum distance between said structure surface and said perforate membrane surface of 2.0 mm, ideally less.

18. A liquid droplet production apparatus according to claim 1 wherein the membrane is supported when not in contact with the actuator by means of a flexible support.

19. A liquid droplet production apparatus according to claim 1 wherein the perforate membrane is stiffened through doming.

20. A liquid droplet production apparatus according to claim 1, wherein the actuator is formed of a generally axisymmetric ring and, wherein the magnetic polarisation is parallel to, or radial and normal to the ring axis of rotational symmetry.

21. A liquid droplet production apparatus according to claim 1, wherein the perforate membrane and liquid containing reservoir form a capsule.

* * * * *